(12) United States Patent
Gordon et al.

(10) Patent No.: US 7,837,729 B2
(45) Date of Patent: Nov. 23, 2010

(54) PERCUTANEOUS MITRAL VALVE ANNULOPLASTY DELIVERY SYSTEM

(75) Inventors: Lucas S. Gordon, Issaquah, WA (US); Mark L. Mathis, Fremont, CA (US); Gregory Nieminen, Bothell, WA (US); Leonard Kowalsky, Bothell, WA (US); Ryan Braxtan, Sammamish, WA (US); Brian J. Doll, Sammamish, WA (US)

(73) Assignee: Cardiac Dimensions, Inc., Kirkland, WA (US)

(*) Notice: Subject to any disclaimer, the term of this patent is extended or adjusted under 35 U.S.C. 154(b) by 1721 days.

(21) Appl. No.: 10/946,332

(22) Filed: Sep. 20, 2004

(65) Prior Publication Data

US 2005/0096666 A1    May 5, 2005

Related U.S. Application Data

(63) Continuation-in-part of application No. 10/331,143, filed on Dec. 26, 2002, now Pat. No. 6,793,673, and a continuation-in-part of application No. 10/313,914, filed on Dec. 5, 2002, now Pat. No. 7,316,708.

(51) Int. Cl.
*A61F 2/06* (2006.01)
(52) U.S. Cl. ..................................................... 623/2.36
(58) Field of Classification Search ................ 606/108, 606/151–157, 191–198; 623/2.36, 1.11–1.54, 623/2.11, 2.37; 600/16–22, 36–38
See application file for complete search history.

(56) References Cited

U.S. PATENT DOCUMENTS 3,974,526 A    8/1976    Dardik et al.
(Continued)

FOREIGN PATENT DOCUMENTS

EP    0893133 A1    1/1999
(Continued)

OTHER PUBLICATIONS

Clifton Alfernss, et al. U.S. Appl. No. 10/429,225, entitled "Device and method for modifying the shape of a body organ," filed May 2, 2003.
(Continued)

*Primary Examiner*—Kevin T Truong
(74) *Attorney, Agent, or Firm*—Shay Glenn LLP

(57) ABSTRACT

The invention is a tissue shaping system, including a tissue shaping device with an expandable anchor and a lock; a delivery catheter; a delivery mechanism adapted to deliver the tissue shaping device from outside a patient to a target site within a lumen within the patient via the delivery catheter; and an actuator adapted to deliver an actuation force to the lock to lock the anchor in an expanded configuration. The invention is also a system adapted to percutaneously deliver and deploy a tissue shaping device at a target site within a lumen of a patient. The system includes: a handle; a delivery mechanism supported by the handle and adapted to deliver the tissue shaping device from outside the patient to the treatment site via a delivery catheter; and an actuator supported by the handle and adapted to deliver an actuation force to lock an anchor of the tissue shaping device in an expanded configuration.

48 Claims, 14 Drawing Sheets

U.S. PATENT DOCUMENTS

| | | | |
|---|---|---|---|
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,662,703 A | 9/1997 | Yurek et al. |
| 5,676,671 A | 10/1997 | Inoue |
| 5,733,325 A | 3/1998 | Robinson et al. |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliott |
| 5,928,258 A | 7/1999 | Khan et al. |
| 5,935,161 A | 8/1999 | Robinson et al. |
| 5,954,761 A | 9/1999 | Machek et al. |
| 5,961,481 A | 10/1999 | Serman et al. |
| 5,961,545 A | 10/1999 | Lentz et al. |
| 5,978,705 A | 11/1999 | KenKnight et al. |
| 5,984,944 A | 11/1999 | Forber |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,053,900 A | 4/2000 | Brown et al. |
| 6,077,295 A | 6/2000 | Limon et al. |
| 6,077,297 A | 6/2000 | Robinson et al. |
| 6,080,182 A | 6/2000 | Shaw et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 * | 6/2002 | Langberg et al. ............ 623/2.36 |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,503,271 B2 | 1/2003 | Duerig et al. |
| 6,537,314 B2 | 3/2003 | Langberg et al. |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,797,001 B2 | 9/2003 | Mathis et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,793,673 B2 | 7/2004 | Kowalsky et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,800,090 B2 | 10/2004 | Alferness et al. |
| 6,805,128 B1 | 10/2004 | Pless et al. |
| 6,824,562 B2 * | 11/2004 | Mathis et al. ............... 623/2.36 |
| 6,827,690 B2 | 12/2004 | Bardy |
| 6,881,220 B2 | 4/2005 | Edwin et al. |
| 6,899,734 B2 | 5/2005 | Castro et al. |
| 6,935,404 B2 | 8/2005 | Duerig et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 7,152,605 B2 | 12/2006 | Khairkhahan et al. |
| 7,175,653 B2 | 2/2007 | Gaber |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0169502 A1 | 11/2002 | Mathis |
| 2002/0183835 A1 | 12/2002 | Taylor et al. |

| | | |
|---|---|---|
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0004572 A1 | 1/2003 | Goble et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0083613 A1 | 5/2003 | Schaer |
| 2003/0088305 A1 | 5/2003 | Van Schie et al. |
| 2003/0105520 A1 | 6/2003 | Alferness et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0171776 A1 | 9/2003 | Adams et al. |
| 2003/0212453 A1 | 11/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter |
| 2004/0176840 A1 | 9/2004 | Langberg |
| 2004/0193191 A1 | 9/2004 | Starksen |
| 2004/0193260 A1 | 9/2004 | Alferness et al. |
| 2004/0220657 A1 | 11/2004 | Nieminen et al. |
| 2004/0243227 A1 | 12/2004 | Starksen et al. |
| 2004/0249452 A1 | 12/2004 | Adams et al. |
| 2004/0260342 A1 | 12/2004 | Vargas et al. |
| 2004/0260384 A1 | 12/2004 | Allen |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0065598 A1 | 3/2005 | Mathis et al. |
| 2005/0085903 A1 | 4/2005 | Lau |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0177228 A1 | 8/2005 | Solem et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0222678 A1 | 10/2005 | Lashinski et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0142854 A1 | 6/2006 | Alferness et al. |
| 2006/0191121 A1 | 8/2006 | Gordon |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| WO | WO98/48717 | 11/1998 |
| WO | WO 98/56435 A1 | 12/1998 |
| WO | WO 00/44313 A1 | 8/2000 |
| WO | WO 00/60995 A2 | 10/2000 |
| WO | WO 00/60995 A3 | 10/2000 |
| WO | WO 00/74603 A1 | 12/2000 |
| WO | WO 01/00111 A1 | 1/2001 |
| WO | WO 01/19292 A1 | 3/2001 |
| WO | WO01/30248 | 5/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |
| WO | WO 2005/046531 | 5/2005 |
| WO | WO 2006/002492 A1 | 1/2006 |

OTHER PUBLICATIONS

Gary Swinford, et al. U.S. Appl. No. 11/276,082, entitled "Device, System and Method to Affect the Mitral Valve Annulus of a Heart," filed Feb. 13, 2006.

Greg Nieminen, et al. U.S. Appl. No. 10/845,474, entitled "Device and method for modifying the shape of a body organ," filed May 12, 2004.

Greg Nieminen, et al. U.S. Appl. No. 11/275,630, entitled "Tissue Shaping Device," filed Jan. 19, 2006.

Mark Mathis, et al. U.S. Appl. No. 10/994,153, entitled "Body lumen device anchor, device and assembly," filed Nov. 19, 2004.

Mathis et al.; U.S. Appl. No. 12/016,054 entitled "Fixed anchor and pull mitral valve device and method," filed Jan. 17, 2008.

Gordon et al.; U.S. Appl. No. 11/971,174 entitled "Medical device delivery system," filed Jan. 8, 2008.

Nieminen et al; U.S. Appl. No. 12/060,781 entitled "Tissue shaping device," filed Apr. 1, 2008.

Pai, Suresh; U.S. Appl. No. 60/329,694 entitled "Percutaneous cardiac support structures and deployment means," filed Oct. 16, 2001.

Mathis et al; U.S. Appl. No. 11/963,417 entitled "Device and method for modifying the shape of a body organ," filed Dec. 21, 2007.

Mathis et al., U.S. Appl. No. 11/782,490 entitled "Device and method for modifying the shape of a body organ, " filed Jul. 24, 2007.

Mathis et al., U.S. Appl. No. 11/782,508, entitled "Device and method for modifying the shape of a body organ, " filed Jul. 24, 2007.

Mathis et al., U.S. Appl. No. 11/782,527 entitled "Device and method for modifying the shape of a body organ, " filed Jul. 24, 2007.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Mark L. Mathis, et al. U.S. Appl. No. 11/279,352, entitled "Mitral Valve Annuloplasty Device with Vena Cava Anchor," filed Apr. 11, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al., "Coronary Sinus Pacing Prevents Induction of Atrial Fibrillation," Circulation 96: 1893-1898, Sep. 16, 1977.

Mathis et al., U.S. Patent Application entitled: "Device and Method for Modifying the Shape of a Body Organ", U.S. Appl. No. 10/429,172 filed May 2, 2003.3

Mathis, Mark; U.S. Appl. No. 11/655,710, entitled "Mitral Valve Device Using Conditioned Shape Memory Alloy," filed Jan. 18, 2007.

Hayner et al.; U.S. Appl. No. 12/189,527 entitled "Catheter cutting tool," filed Aug. 11, 2008.

El-Maasarany et al.; The coronary sinus conduit function: Anatomical study (relationship to adjacent structures); http://europace.oxfordjournals.org/cge/content/full/7/5/475.

Yamanouchi, et al.; Activation Mapping from the coronary sinus may be limited by anatomic variations; vol. 21 pp. 2522-2526; Nov. 1998.

* cited by examiner

PERCUTANEOUS MITRAL VALVE ANNULOPLASTY DELIVERY SYSTEM

CROSS-REFERENCE

This application is a continuation-in-part of U.S. patent application Ser. No. 10/313,914, filed Dec. 5, 2002, now U.S. Pat. No. 7,316,708; and U.S. patent application Ser. No. 10/331,143, filed Dec. 26, 2002, now U.S. Pat. No. 6,793,673; which applications are incorporated herein by reference in their entirety and to which applications we claim priority under 35 USC §120.

BACKGROUND OF THE INVENTION

The invention relates generally to percutaneous delivery systems for tissue shaping devices intended to be delivered through a lumen to a site within a vessel of the patient to modify target tissue adjacent to the vessel. In particular, the invention relates to delivery systems for percutaneous mitral valve annuloplasty devices and methods for using the same.

Tissue shaping devices for treating mitral valve regurgitation have been described. See, e.g., U.S. patent application Ser. No. 10/142,637 (now U.S. Pat. No. 6,824,562), "Body Lumen Device Anchor, Device and Assembly;" U.S. patent application Ser. No. 10/331,143 (now U.S. Pat. No. 6,793,673), "System and Method to Effect the Mitral Valve Annulus of a Heart;" U.S. patent application Ser. No. 10/429,172, "Device and Method for Modifying the Shape of a Body Organ;" and U.S. patent application Ser. No. 10/742,516, "Tissue Shaping Device With Conformable Anchors." These devices are intended to be delivered percutaneously to a site within a patient's coronary sinus and deployed to reshape the mitral valve annulus adjacent to the coronary sinus.

During deployment of such tissue shaping devices one or more anchors may need to be expanded and locked using actuation forces delivered from outside the patient. Thus, the percutaneous delivery and deployment of tissue shaping devices may require the physician to perform remote operations on the device and on the patient through the device. What is needed, therefore, is a delivery system that permits the physician to perform these tasks.

SUMMARY OF THE INVENTION

The present invention provides a tissue shaping delivery system and method. One aspect of the invention is a tissue shaping system including a tissue shaping device with an expandable anchor and a lock; a delivery catheter; a delivery mechanism (including, e.g., a pusher) adapted to deliver the tissue shaping device from outside a patient to a target site within a lumen within the patient via the delivery catheter; and an actuator adapted to deliver an actuation force to the lock to lock the anchor in an expanded configuration. In some embodiments, the invention includes a cartridge adapted to contain the tissue shaping device, the delivery mechanism being further adapted to deliver the tissue shaping device from the cartridge to the delivery catheter. The tissue shaping system may also include a dye port adapted to admit an imaging contrast agent to the lumen, such as during delivery and deployment of the tissue shaping device. The dye port may be part of a connector extending from a proximal end of the delivery catheter, with the connector also including a device port, the delivery mechanism being further adapted to delivery the tissue shaping device from outside the patient to the delivery catheter through the device port.

In some embodiments the tissue shaping system includes a handle associated with the delivery mechanism. The handle may be adapted to support the actuator. In embodiments in which the system includes a cartridge adapted to contain the tissue shaping device, the cartridge may be further adapted to engage the handle during delivery and/or deployment of the tissue shaping device.

In some embodiments of the tissue shaping system, the actuator is further adapted to operate the delivery mechanism to move the tissue shaping device with respect to the delivery catheter to, e.g., expose or recapture the anchor. In some embodiments, the actuator is a rotating nut.

In some embodiments of this aspect of the invention the actuator is adapted to move the delivery catheter distally to lock the anchor. In other embodiments the tissue shaping system may also include a locking sleeve, the actuator being further adapted to move the locking sleeve distally to lock the anchor.

In some embodiments the tissue shaping system includes an attachment mechanism adapted to attach the tissue shaping device to the delivery mechanism, such as a tether attached to the tissue shaping device. The attachment mechanism may be further adapted to release the tissue shaping device from the delivery mechanism, such as through the use of a hitch wire and a tether attached to the tissue shaping device. The attachment mechanism may also include a hitch wire actuator adapted to move the hitch wire to release the tether from the device and/or a device release interlock adapted to prevent release of the device prior to actuating the anchor lock actuator.

In some embodiments of the tissue shaping system, the tissue shaping device further includes a second anchor, the actuator being further adapted to deliver an actuation force to a second anchor lock to lock the second anchor in an expanded configuration. The system may alternatively have a second actuator, the second actuator being further adapted to deliver an actuation force to the second anchor lock to lock the second anchor in an expanded configuration. A handle may support the first and second actuators.

Another aspect of the invention provides a system adapted to percutaneously deliver and deploy a tissue shaping device at a target site within a lumen of a patient, including: a handle; a delivery mechanism (possibly including a pusher) supported by the handle and adapted to deliver the tissue shaping device from outside the patient to the treatment site via a delivery catheter; and an actuator supported by the handle and adapted to deliver an actuation force to lock an anchor of the tissue shaping device in an expanded configuration. In some embodiments the handle has a cartridge interface adapted to mate with a cartridge containing a tissue shaping device, and the delivery system may be further adapted to deliver the tissue shaping device from a delivery catheter to the target site when a tissue shaping device cartridge engages the cartridge interface. In some embodiments, the actuator may include the cartridge interface. In some embodiments the actuator may include a rotating member with threads adapted to mate with threads on a cartridge.

In some embodiments the system includes a locking sleeve, the actuator being further adapted to move the locking sleeve distally to lock the anchor. The handle may include a channel, with the actuator being disposed in the channel, and the actuator may include an actuator lock adapted to prevent movement of the actuator within the channel.

In some embodiments the system includes a device attachment mechanism supported by the handle and adapted to attach the tissue shaping device to the handle. The attachment mechanism may include a tether attached to the handle and/or a hitch wire attached to the handle. In embodiments with a hitch wire the attachment mechanism further may a hitch wire actuator adapted to move the hitch wire to release the device and possibly a device release interlock adapted to prevent operation of the hitch wire actuator prior to actuating the anchor lock actuator.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While the invention relates to methods and devices for delivering tissue shaping devices generally, the invention will be described with respect to tissue shaping devices delivered to the coronary sinus of the heart to reshape the mitral valve annulus to treat mitral valve regurgitation. As used herein, "coronary sinus" includes the great cardiac vein as well as the coronary sinus of the heart.

Figure 1:
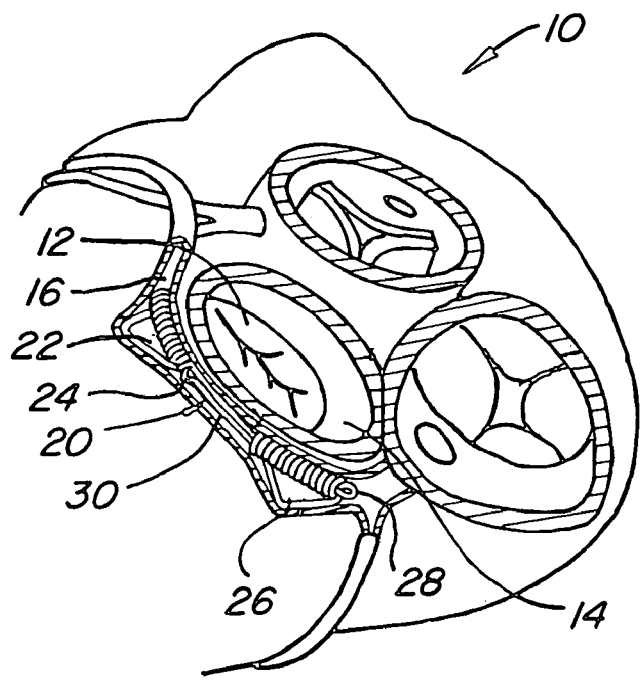
FIG. 1 is a cross-sectional view of a human heart showing a tissue shaping device in the lumen of the coronary sinus.

FIG. 1 shows a cross-section of a human heart 10 with the atria removed to show the mitral valve 12, the mitral valve annulus 14 and the coronary sinus 16. A tissue shaping device 20 in the form of a percutaneous mitral valve annuloplasty device is disposed within the coronary sinus to reshape the mitral valve annulus 14 to provide for improved coaptation of the mitral valve leaflets. As shown, tissue shaping device 20 has an expandable distal anchor 22, a distal anchor lock 24, an expandable proximal anchor 26, a proximal anchor lock 28, and a connector 30 extending between the distal and proximal anchors. Proximal anchor lock 28 has serves as a delivery system attachment mechanism, as explained below.

Figure 2:
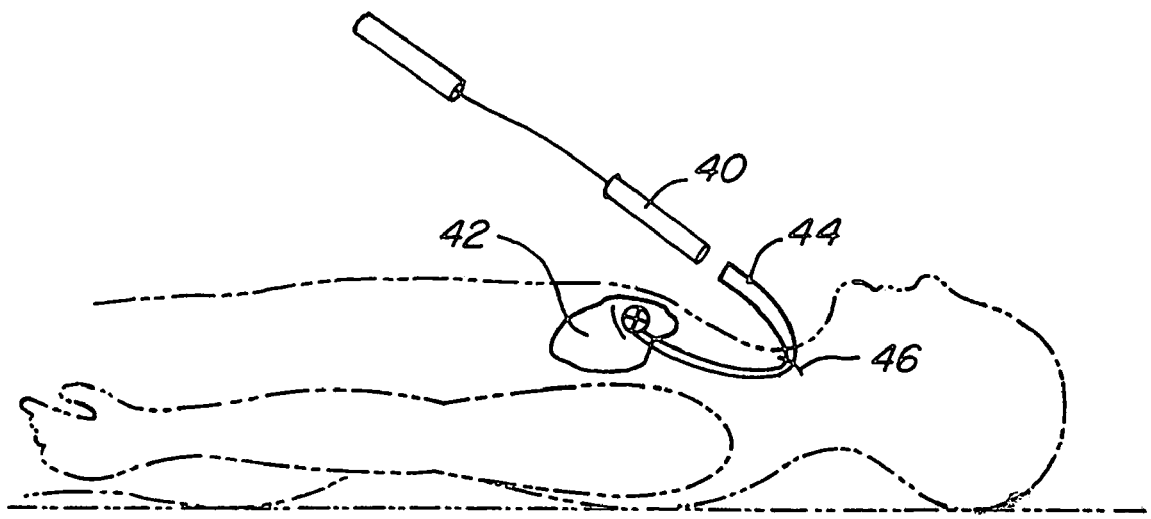
FIG. 2 is a schematic view of a tissue shaping device delivery system according to this invention.

FIG. 2 is a schematic drawing showing the general elements of a delivery system 40 adapted to delivering and deploying a tissue shaping device to a target site within the lumen of a vessel in or around a patient's heart 42. A delivery catheter 44 has been inserted through an opening 46 formed in the patient's jugular vein or other blood vessel and advanced into the heart. Delivery system 40 interacts with delivery catheter 44 to deliver and deploy the tissue shaping device at the target site within the patient.

Figure 3:
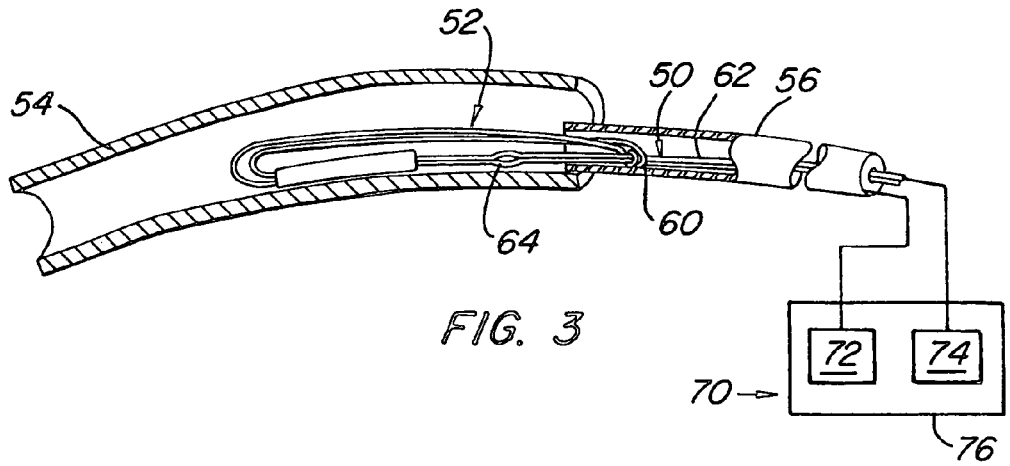
FIG. 3 is a cross-sectional view showing a step in the delivery and deployment of a tissue shaping device according to this invention.

FIGS. 3-6 show steps from the delivery and deployment of a tissue shaping device having at least one anchor similar to the anchors of device 20 of FIG. 1. In FIG. 3, a tissue shaping device 50 has been delivered to a target site within the lumen of a vessel 54 via a delivery catheter 56. FIG. 3 shows an expandable anchor 52 of tissue shaping device 50 beginning to emerge from catheter 56. In this embodiment, this action is due to proximal movement of catheter 56 while device 50 is held stationary. In alternative embodiments, the device could be delivered from the distal end of the catheter by pushing the device distally while holding the catheter stationary or a combination of distal movement of the device and proximal movement of the catheter. Anchor 52 is shown in a collapsed, unexpanded configuration.

A delivery system 70 provides the mechanisms to deliver and deploy device 50 from outside the patient. Actuator 72 and delivery mechanism 74 associated with catheter 56 and device 50, respectively, provide for the relative movement between device 50 and catheter 56. For example, delivery mechanism 74 may be a pusher used to advance device 50 down catheter 56 to the target site shown in FIG. 3, and actuator 72 can be used to pull catheter 56 proximally while delivery mechanism 74 holds device 50 stationary within vessel 54. Actuator 72 and delivery mechanism 74 may be supported by a handle or other housing 76.

Figure 4:
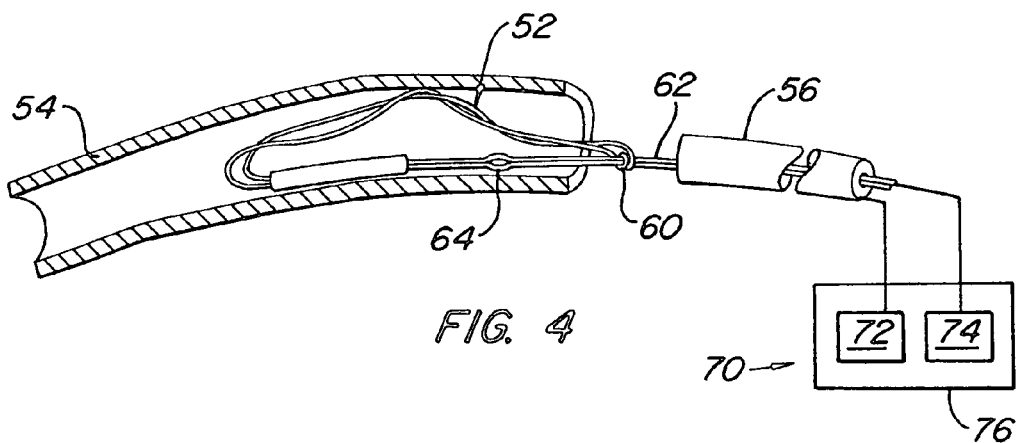
FIG. 4 is a cross-sectional view showing another step in the delivery and deployment of a tissue shaping device according to this invention.

In FIG. 4, catheter 56 has been pulled further proximally by actuator 72 so that anchor 52 is completely outside of catheter 56 and has started to self-expand. In this embodiment, anchor 52 is formed from a shape memory material (such as Nitinol) and has been treated so as to expand upon emergence from the catheter.

Figure 5:
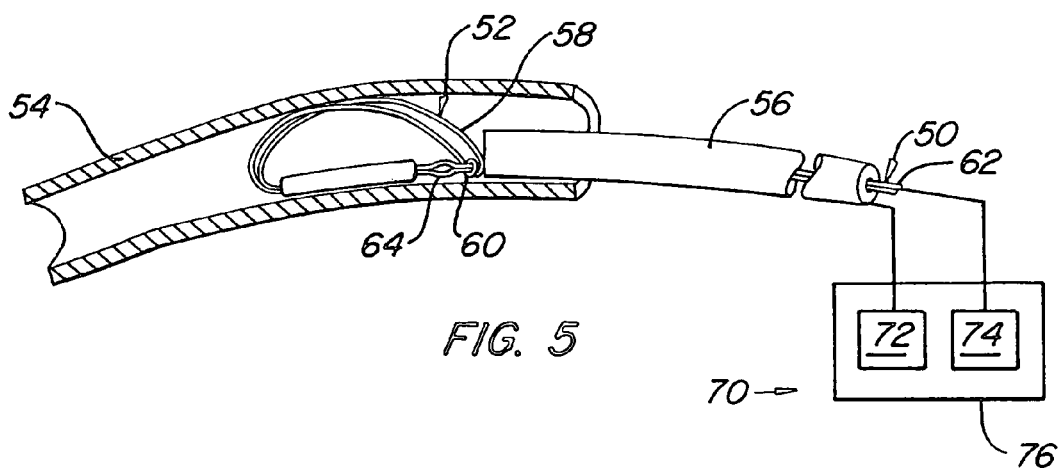
FIG. 5 is a cross-sectional view showing another step in the delivery and deployment of a tissue shaping device according to this invention.
Figure 6:
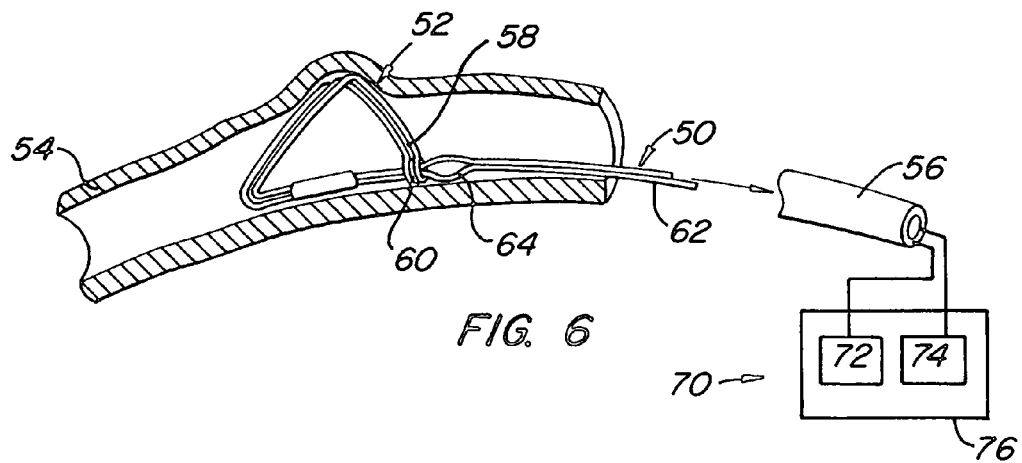
FIG. 6 is a cross-sectional view showing another step in the delivery and deployment of a tissue shaping device according to this invention.

FIGS. 5 and 6 show how the delivery system may be used to further expand and lock anchor 52. Formed in the proximal side 58 of anchor 52 is a loop 60 encircling a proximally extending connector 62. Connector 62 may connect with other elements at the proximal side of device 50, such as a second anchor, depending on device design. As shown in FIG. 5, while delivery mechanism 74 holds device 50 stationary, actuator 72 has moved delivery catheter 56 distally to engage the proximal side 58 of anchor 52 and to move it distally to further expand anchor 52.

As shown in FIG. 6, further distal movement of delivery catheter 56 with respect to device 50 has pushed loop 60 distally over a lock bump 64. Lock bump 64 cams inward in response to the distal force of loop 60, then returns to its prior shape to hold loop 60 distal to lock bump 64. Delivery catheter may then be moved proximally to perform other functions or to be removed from the patient.

Figure 7:
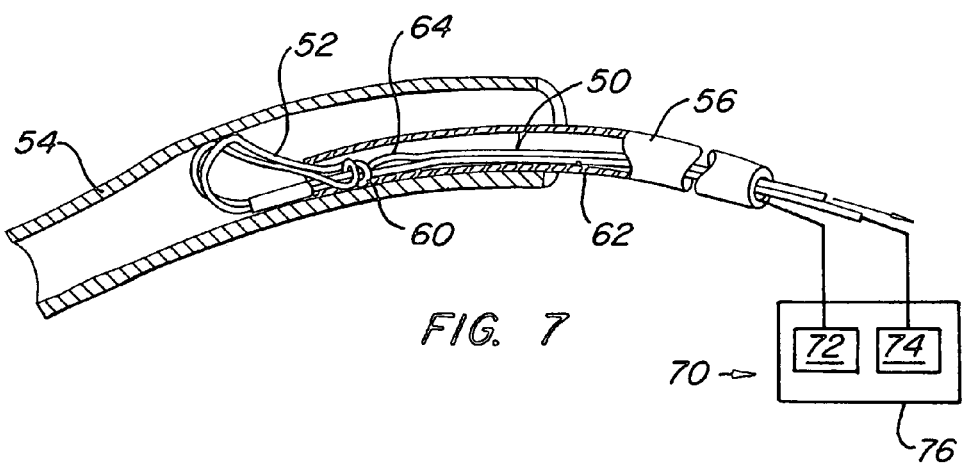
FIG. 7 is a cross-sectional view showing a step in the recapture of a tissue shaping device according to this invention.
Figure 8:
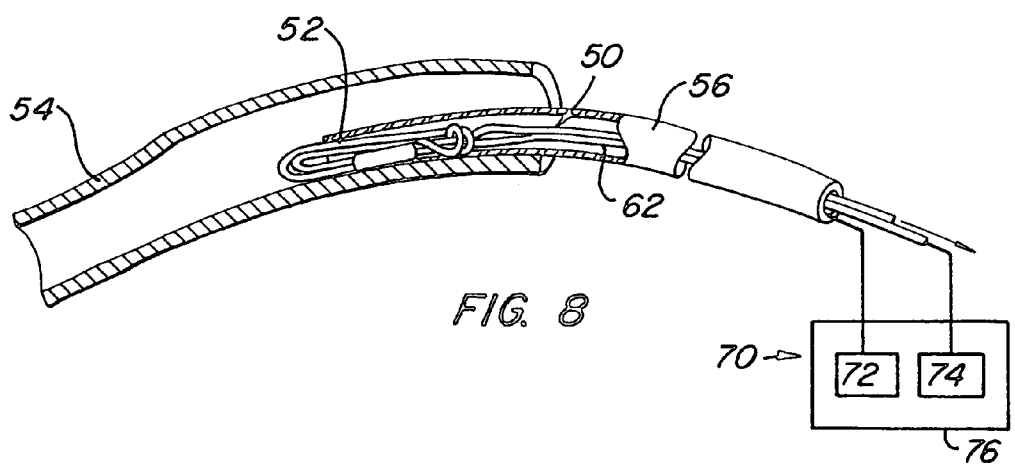
FIG. 8 is a cross-sectional view showing a step in the recapture of a tissue shaping device according to this invention.

After deployment of a tissue shaping device, it may become necessary to reposition the device or to remove the device from the patient. FIGS. 7 and 8 demonstrate the recapture of tissue shaping device 50 back into delivery catheter 56 after delivery and deployment.

In FIG. 7, delivery mechanism 74 holds device 50 stationary while delivery catheter 56 is advanced distally against anchor 52 by actuator 72. The actuation force against anchor 52 collapses the anchor, allowing delivery catheter to recapture the device as shown in FIG. 8. The catheter and device can then be removed from the patient or moved to another target site.

Figure 9:
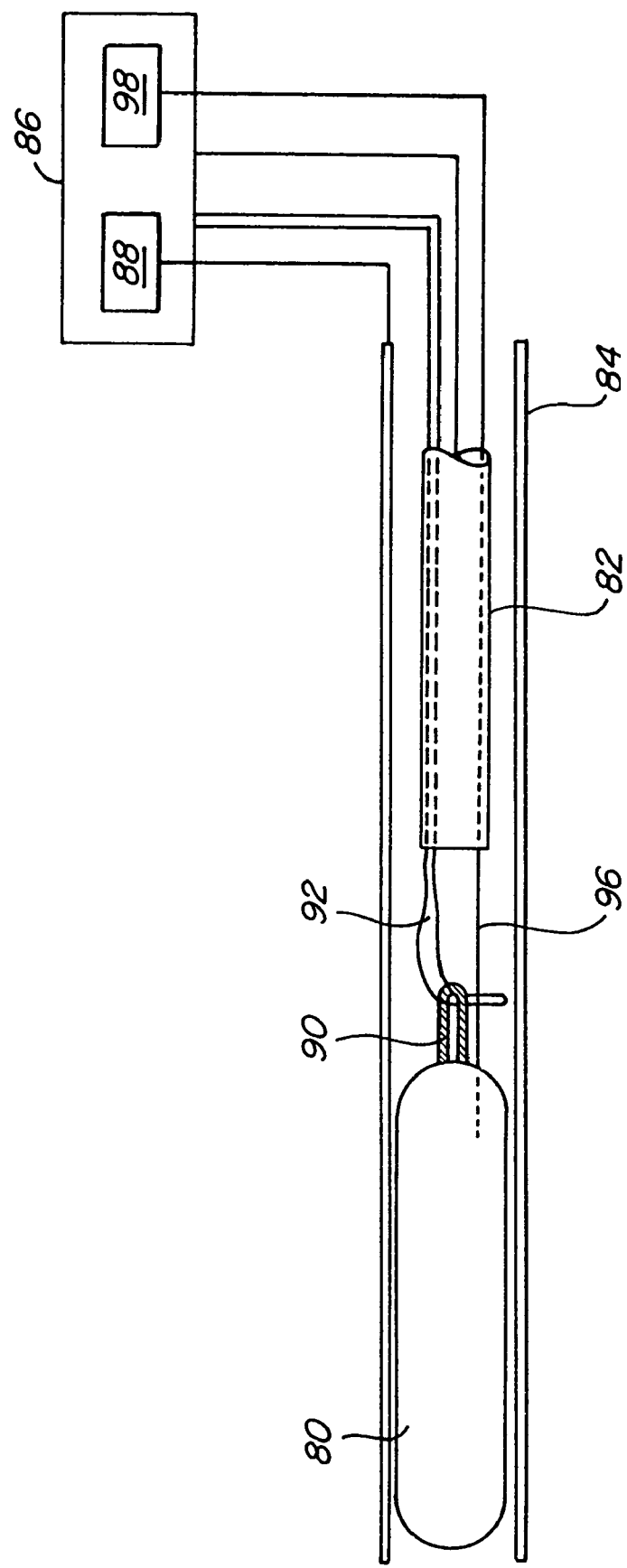
FIG. 9 shows an attachment mechanism for a tissue shaping device delivery system.

FIG. 9 shows an attachment mechanism between a tissue shaping device 80 and a delivery mechanism, such as pusher 82, within a delivery catheter 84. Pusher extends outside of the patient and is attached to a handle or other housing 86, such as through an actuator. Pusher 82 may be operated by an actuator or by the handle itself to advance device 80 distally through catheter 84 or to hold device 80 stationary against a proximal force exerted on device 80, such as when delivery catheter 84 is withdrawn proximally by an actuator 88.

Device 80 has an attachment eyelet 90. A tether 92 extending down pusher 82 has a loop 94 formed at its distal end. The proximal ends of tether 92 are preferably attached to handle 86. Loop 94 extends through eyelet 90, and a hitch wire 96 passes through loop 94 and into the proximal end of device 80 as shown, thereby preventing loop 94 from being withdrawn from eyelet 90. Tether 92 can be used to pull device 80 proximally or to hold device 80 stationary against a distal force exerted on device 80, such as during recapture. Tether 92 may also be used to hold device 80 tightly against pusher 82 during delivery and deployment of the device.

To release device 80 from the delivery mechanism, hitch wire 96 may be disengaged from device 80. In this embodiment, hitch wire 96 is disengaged by moving the hitch wire proximally through the action of a hitch wire actuator 98 while holding device 80 stationary with pusher 92. When hitch wire 96 is disengaged from device 80 and moved proximal to the loop of tether 92, proximal movement of tether 92 will pull the tether's loop out of eyelet 90.

Figure 10:
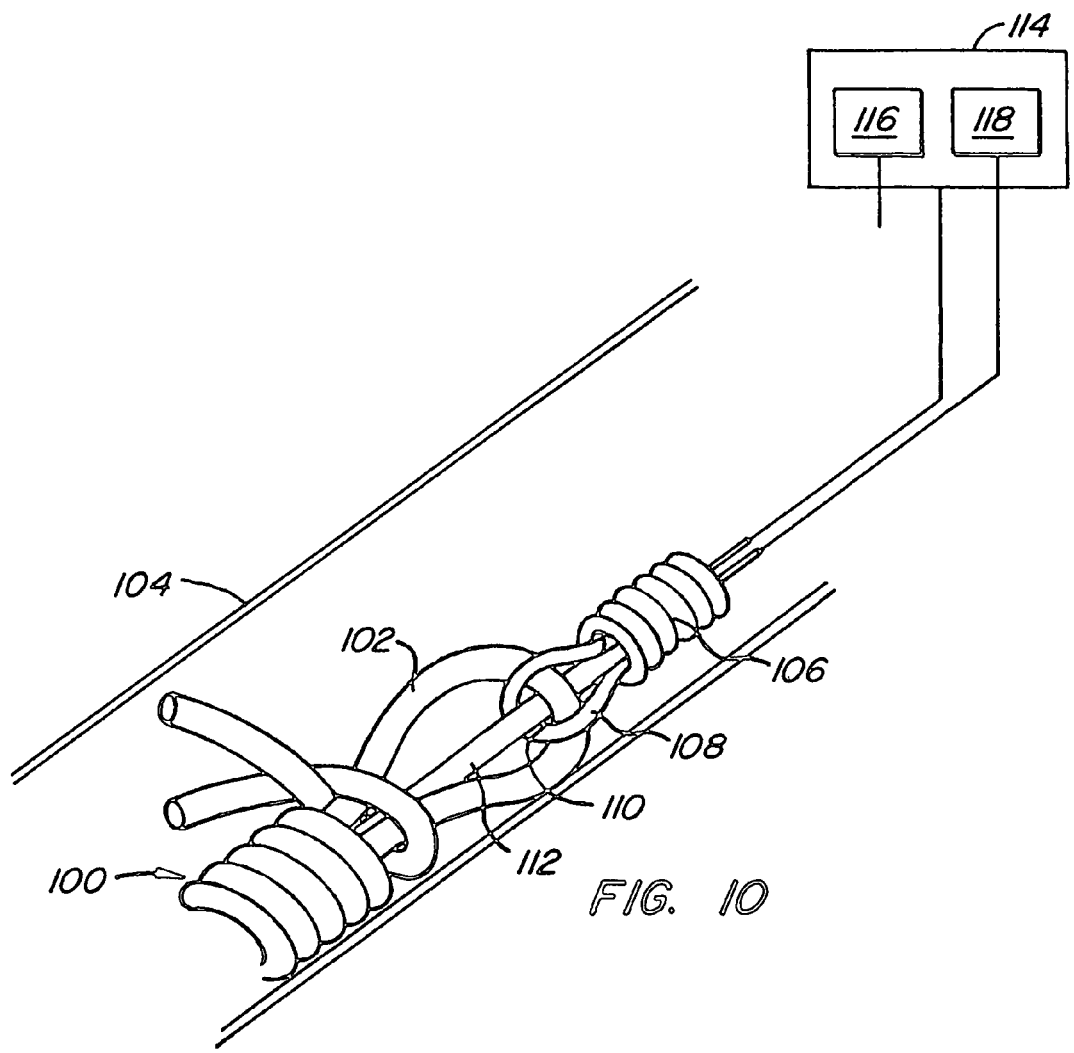
FIG. 10 shows another attachment mechanism for a tissue shaping device delivery system.

FIG. 10 shows another attachment mechanism for a tissue shaping device and its delivery mechanism. As in the embodiment of FIG. 9, an eyelet 102 extends proximally from tissue shaping device 100 within delivery catheter 104. The distal end of pusher 106 has an eyelet 108 at its distal end that overlaps with device eyelet 102 to form an overlap opening 110. A hitch wire 112 extends through pusher 106 and overlap opening 110 into the proximal end of tissue shaping device 100.

As in the previous embodiment, catheter 104, pusher 106 and hitch wire 112 extend out of the patient to a handle or other housing 114. Pusher 106 may be operated by an actuator or by handle 114 to advance device 100 distally through catheter 104 or to hold device 100 stationary against a proximal force exerted on device 100, such as when delivery catheter 104 is withdrawn proximally by an actuator 116 supported by handle 114. Also, because the attachment mechanism of this embodiment holds pusher 106 against device 100, pusher 106 can be used to pull device 100 proximally or to hold device 100 stationary against a distal force exerted on device 100, such as during recapture.

To release device 100 from the delivery mechanism, hitch wire 112 may be disengaged from device 100. As in the embodiment of FIG. 9, hitch wire 112 is disengaged by moving the hitch wire proximally through the action of a hitch wire actuator 118 while holding device 100 stationary with pusher 106. When hitch wire 112 is disengaged from device 100 and moved proximal to the overlap opening 110, device 100 is disengaged from the delivery mechanism.

Figure 11:
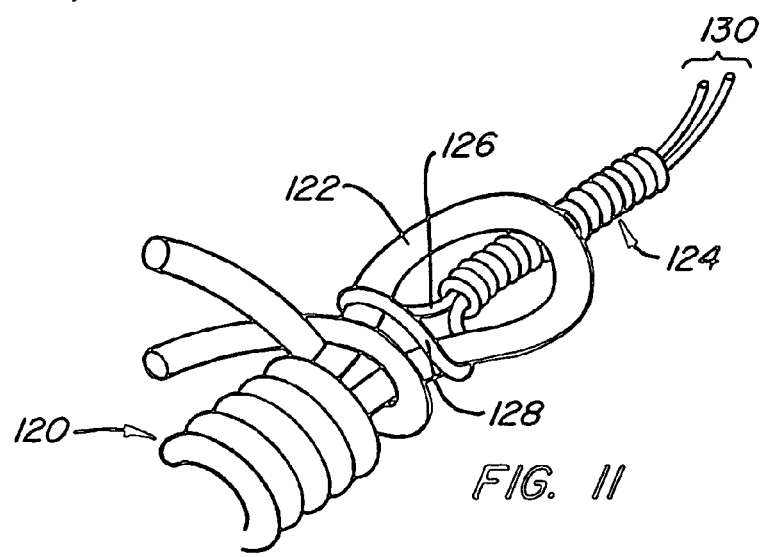
FIG. 11 shows yet another attachment mechanism for a tissue shaping device delivery system.

FIG. 11 shows an attachment mechanism that can be used to engage a tissue shaping device after initial deployment for possible recapture of the device. As in other embodiments, device 120 has a proximal eyelet 122. Retractor 124 has a cable 126 extending through it. Cable 126 has a loop 128 at its distal end and free ends 130 extending out of the patient, possibly to a handle or housing (not shown). To engage device 120, retractor 124 and looped cable 126 are advanced to device 120 with loop 128 arranged to be large enough to surround eyelet 122. When loop 128 passes over and around eyelet 122, one or both of the free ends of cable 126 are pulled proximally to pull loop 128 tightly about eyelet 122, as shown. Retractor 124 may then be used to pull device 120 proximally, such as for recapture into a catheter. Alternatively, retractor may be used as a pusher to apply a distally directed force on device 120, if needed.

Figure 12:
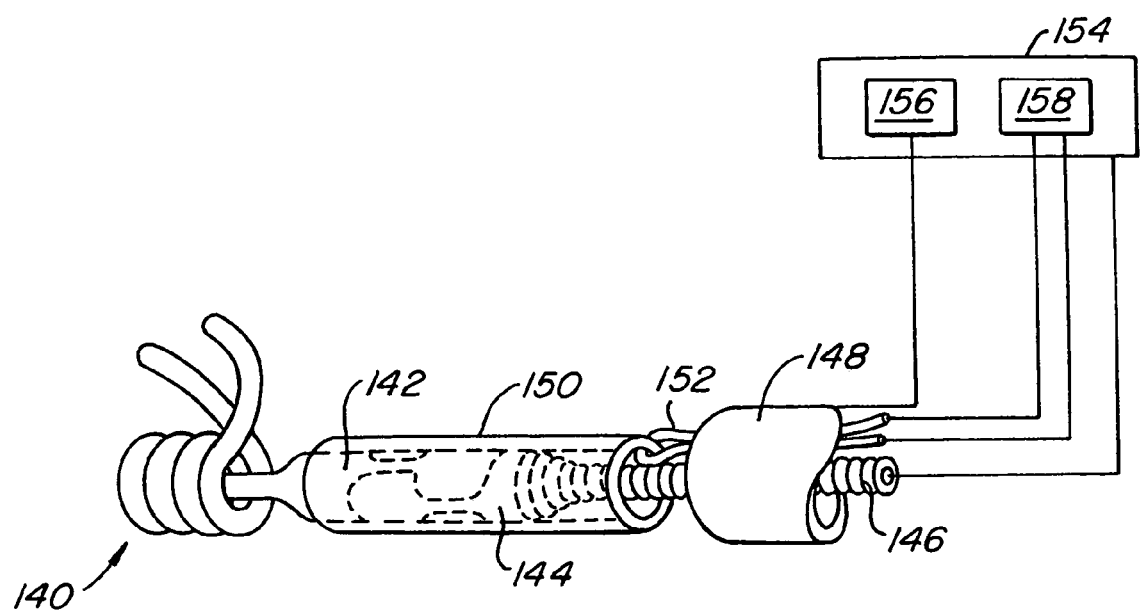
FIG. 12 shows still another attachment mechanism for a tissue shaping device delivery system.
Figure 13:
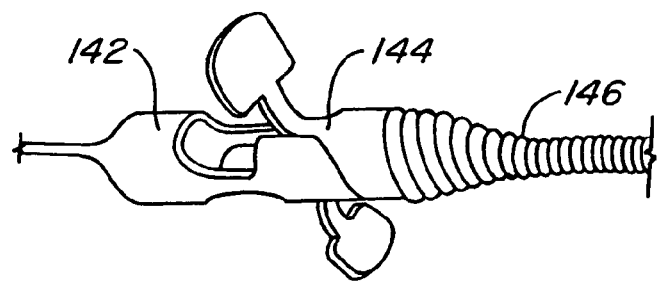
FIG. 13 is a detail of the attachment mechanism of FIG. 12 in a disengaged configuration.

FIGS. 12 and 13 show yet another attachment mechanism between a tissue shaping device and a delivery mechanism. Tissue shaping device 140 has a locking structure 142 at its proximal end designed to mate with a corresponding locking structure 144 at the distal end of a pusher 146 within catheter 148. A cover 150 is disposed over the interlocked locking structures to maintain the connection between device 140 and pusher 146. A tether 152 is connected to cover 150.

Catheter 148, pusher 146 and tether 152 extend out of the patient to a handle or other housing 154. Pusher 146 may be operated by an actuator or by handle 154 to advance device 140 distally through catheter 148 or to hold device 140 stationary against a proximal force exerted on device 140, such as when delivery catheter 148 is withdrawn proximally by an actuator 156 supported by handle 154. Also, because the attachment mechanism of this embodiment holds pusher 146 against device 140, pusher 146 can be used to pull device 140 proximally or to hold device 140 stationary against a distal force exerted on device 140, such as during recapture.

To release device 140 from the delivery mechanism, tether 152 may be pulled proximally to pull cover 150 off of the locking structures 142 and 144, such as by use of an actuator 158, while holding device 100 stationary with pusher 146. Locking structures 142 and 144 are preferably formed from a shape memory material. When cover 150 is removed from the locking structures, the locking structures assume an unstressed configuration such as that shown in FIG. 13, thereby disengaging device 140 from pusher 146.

Figure 14:
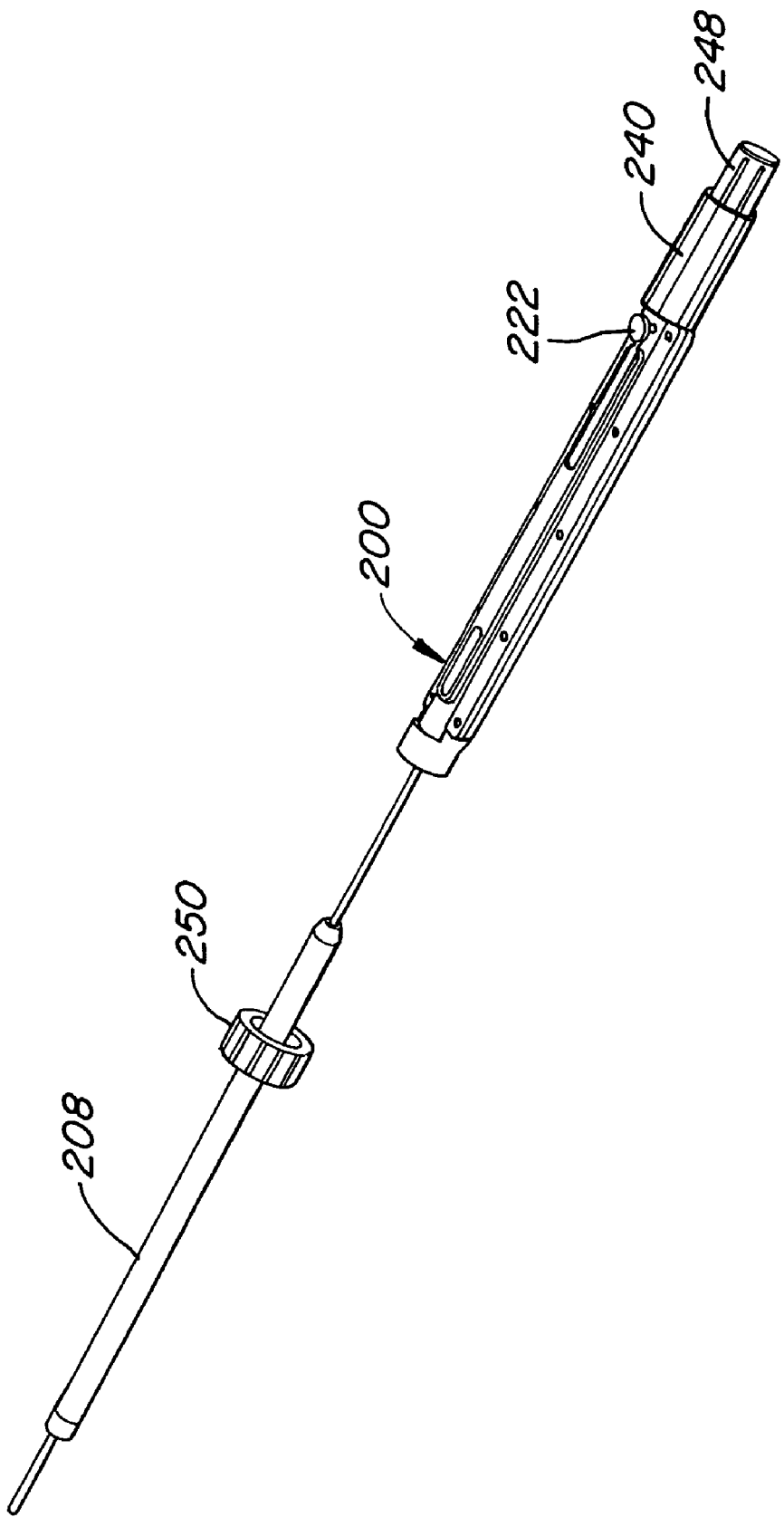
FIG. 14 is a perspective view of a tissue shaping device delivery system according to this invention.

FIGS. 14-21 show a tissue shaping device delivery and deployment system according to one embodiment of this invention. The system includes a handle 200 supporting delivery, deployment and attachment mechanisms for a tissue shaping device 202 having distal and proximal expandable anchors 204 and 206, respectively. In FIG. 14, the device is disposed in a compressed configuration within a cartridge 208. In this embodiment, the device will go directly from cartridge 208 into a delivery catheter for delivery and deployment in a patient.

Figure 15:
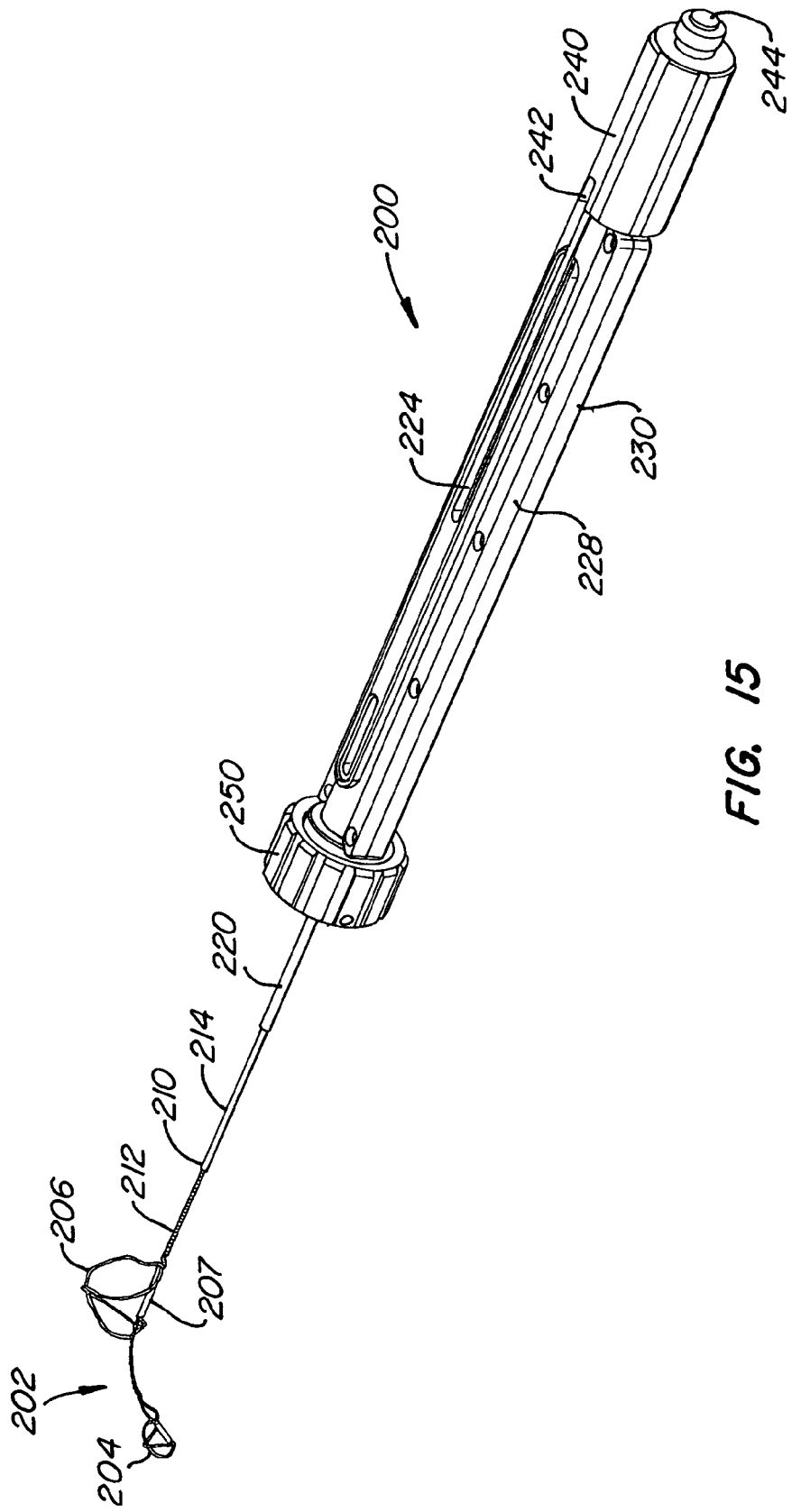
FIG. 15 is another perspective view of the tissue shaping device delivery system of FIG. 14 showing a tissue shaping device without a cartridge.

As shown in FIG. 15, a pusher 210 abuts the proximal end of tissue shaping device 202. Pusher 210 should be flexible and incompressible, and its properties may vary from section to section along its length. In one embodiment, pusher 210 is formed at its distal end from a coiled spring 212 (e.g., to facilitate bending) and thereafter from a stainless steel hypotube 214. Device 202 is attached to pusher 210 via a tether 216 and hitch wire 218 in an arrangement such as that described above with respect to FIG. 9. The tether has to be strong enough to apply an appropriate proximally directed force during delivery, deployment and recapture; the hitch wire has to be stiff enough not to kink or pull through the eyelet when the tether is pulled proximally. For example, for use in a tissue shaping system intended to treat mitral valve regurgitation via the coronary sinus, the tether preferably can pull up to 18 pounds. In one embodiment, tether 216 is formed from 0.007 inch stainless steel with a full hard temper, and hitch wire is formed from 0.011 inch 304 stainless steel. Tether 216 and hitch wire 218 extend through the pusher's lumen. Pusher 210, tether 216 and hitch wire 218 are attached to and supported by handle 200, as discussed below with respect to FIGS. 17 and 18.

Figure 16:
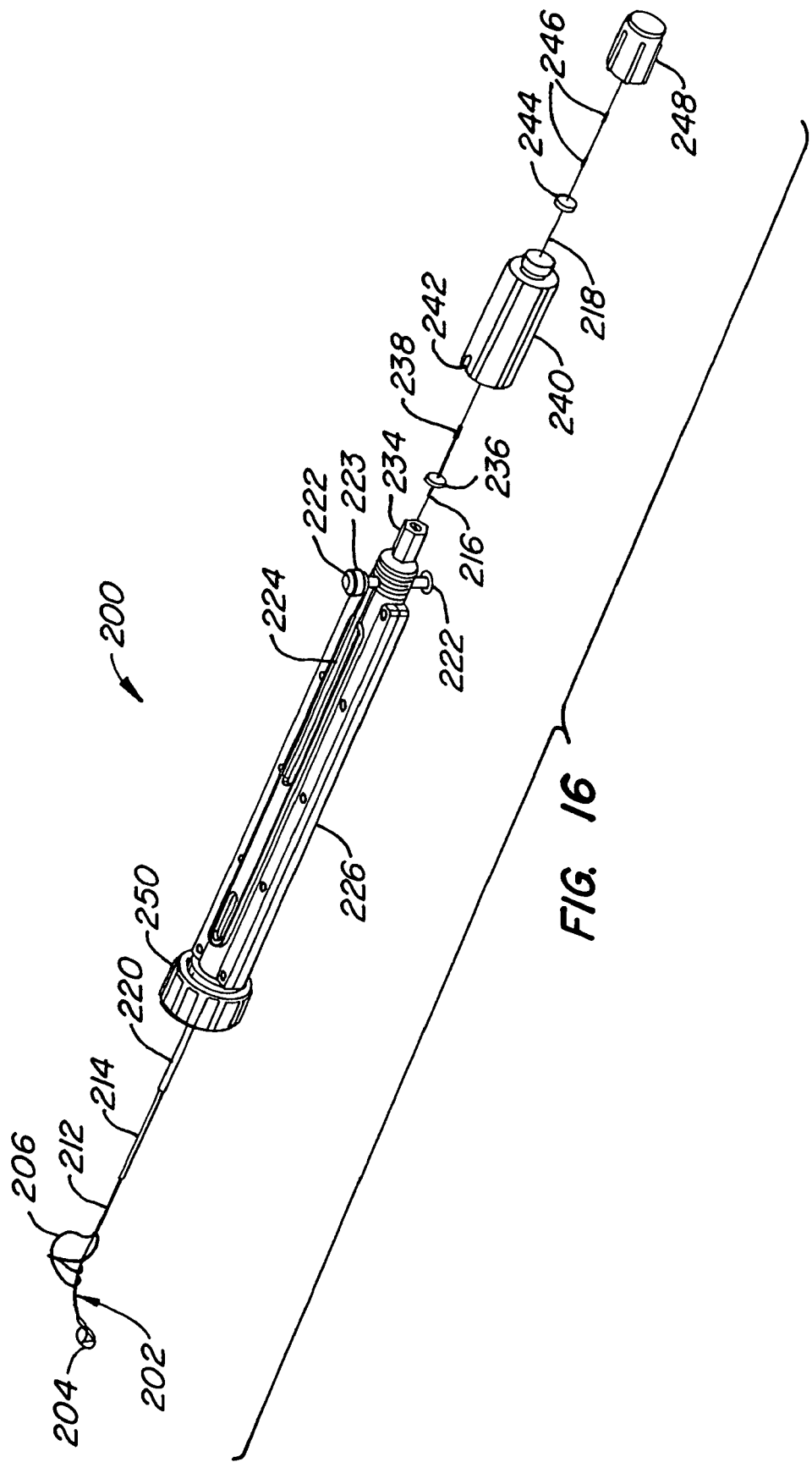
FIG. 16 is an exploded view of the tissue shaping device and delivery system of FIG. 15.
Figure 17:
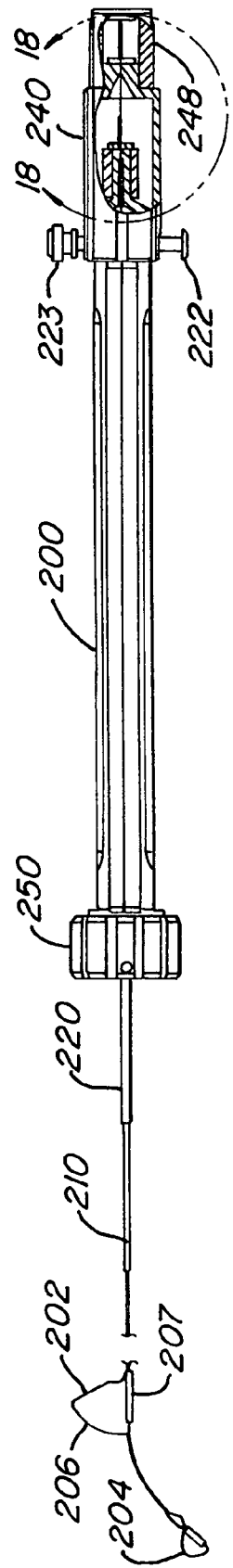
FIG. 17 is a partial cross-sectional view of certain portions of the tissue shaping device delivery system of FIG. 15.

Surrounding pusher 210 is a locking sleeve 220 whose inner diameter is close to the outer diameter of pusher 210 in order to minimize backflow of blood or other fluids. The proximal end of locking sleeve 220 is supported by a slider (not shown) resting in a circular track formed by the handle housing. Actuator knobs 222 are threaded into holes formed in the sides of the slider, and the slider and actuator knobs are attached to the locking sleeve 220 by adhesive. One of the actuator knobs may be provided with an actuation interlock, such as a screw down portion 223 that screws against the handle housing to prevent movement of the actuator knobs and locking sleeve. As shown in FIG. 16, actuator knobs 222 fit in tracks 224 formed in handle 200.

Figure 18:
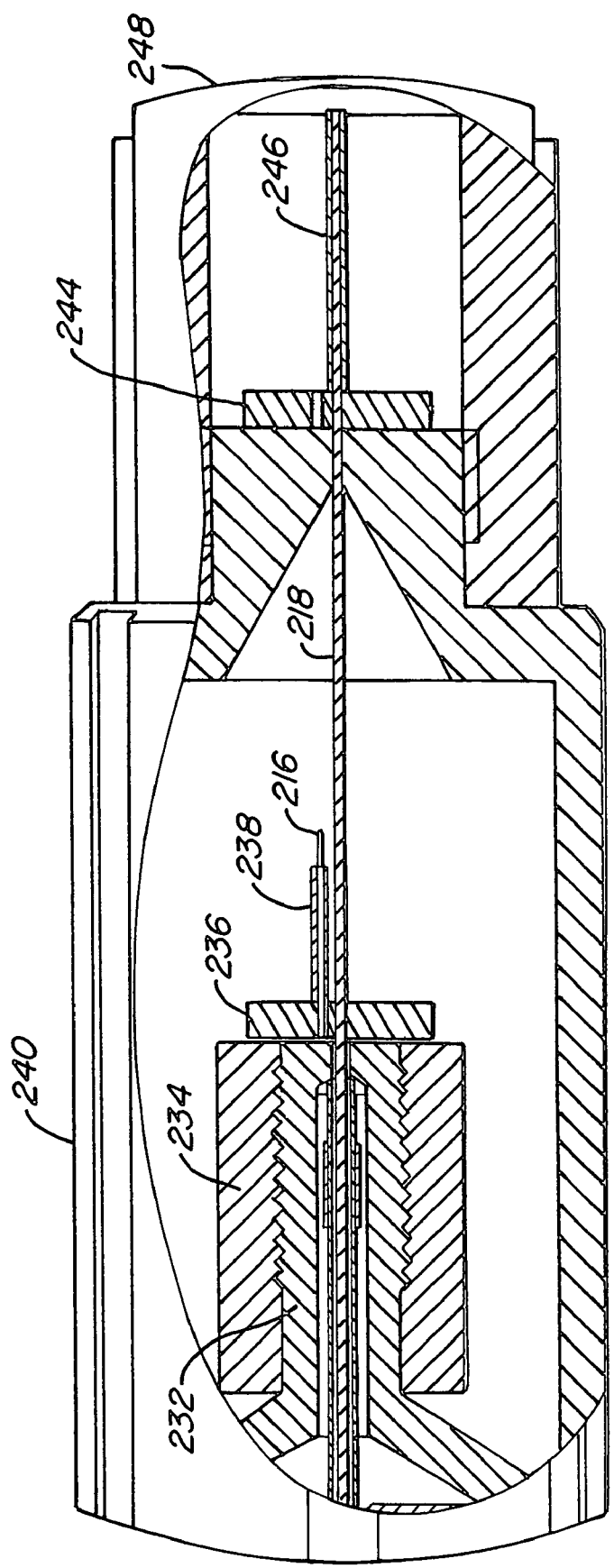
FIG. 18 is a detailed cross-sectional view of a portion of the tissue shaping device shown in FIG. 17.

When assembling the delivery system, pusher 210 is placed within locking sleeve 220. Handle housing 226 has two parts, 228 and 230, which are placed and screwed together around the locking sleeve and pusher. As shown in FIG. 18, assembly of the two halves of handle housing 226 attaches the proximal end of pusher 210 to handle 200 with a press fit connection (which may be supplemented with adhesive) in a pusher connection area 232 of handle housing 226. Locking sleeve actuator knobs 222 are in the tracks 224, as discussed above.

Hitch wire 218 and tether 216 are then threaded into the central lumen of pusher 210, and device 202 is attached by placing the looped end of tether 216 through an eyelet (not shown) on the proximal end of device 202. Hitch wire 218 passes through the looped end of tether 216 into the device's proximal anchor crimp tube 207. (Placement of the distal end of the hitch wire inside the crimp tube helps prevent injury to the patient's heart or blood vessels by the hitch wire.)

Tether 216 and hitch wire 218 extend proximally from the proximal end of pusher 210 through the proximal end of pusher connection area 232 and through holes formed in a disc 236 disposed proximal to pusher connection area 232 and jack nut 234. A crimp tube 238 or other connector attaches to the proximal end of tether 216 to prevent it from passing distally through disc 236; excess portions of tether 216 may be cut off. A jack nut 234 threaded around the outside of pusher connection area 232 may then be rotated about pusher connection area 232 to move jack nut 234, disc 236 and crimp tube 238 proximally with respect to the handle housing, thereby tightening tether 216 and pulling device 202 tight against pusher 210.

A release knob 240 is threaded onto handle housing 226 around pusher connection area 232 with track portions 242 lining up with handle tracks 224, as shown. Hitch wire 218 extends proximally through release knob 240 and a second disc 244, and the proximal end of hitch wire 218 is crimped with one or more crimp tubes 246 to prevent distal movement of hitch wire 218 with respect to the handle. A cap 248 covers the distal end of hitch wire 218 to prevent injury to the user from the sharp wire end.

Prior to delivery and deployment, the eyelet of the proximal anchor 206 is pulled proximally over the pusher coil 212, and the eyelet of the distal anchor is pulled proximally over the connector between the two anchors. Device 202 is then compressed and loaded into cartridge 208 with the distal anchor 204 at the distal end of the cartridge and with the pusher, tether and hitch wire extending from the proximal end of cartridge 208 into handle 200. A loading tool, such as a two-piece funnel, may be used to assist in the compression and loading of the device into the cartridge. In a preferred embodiment, a control nut 250 is threaded onto the threaded exterior of cartridge 208, as shown in FIG. 14.

Figure 19:
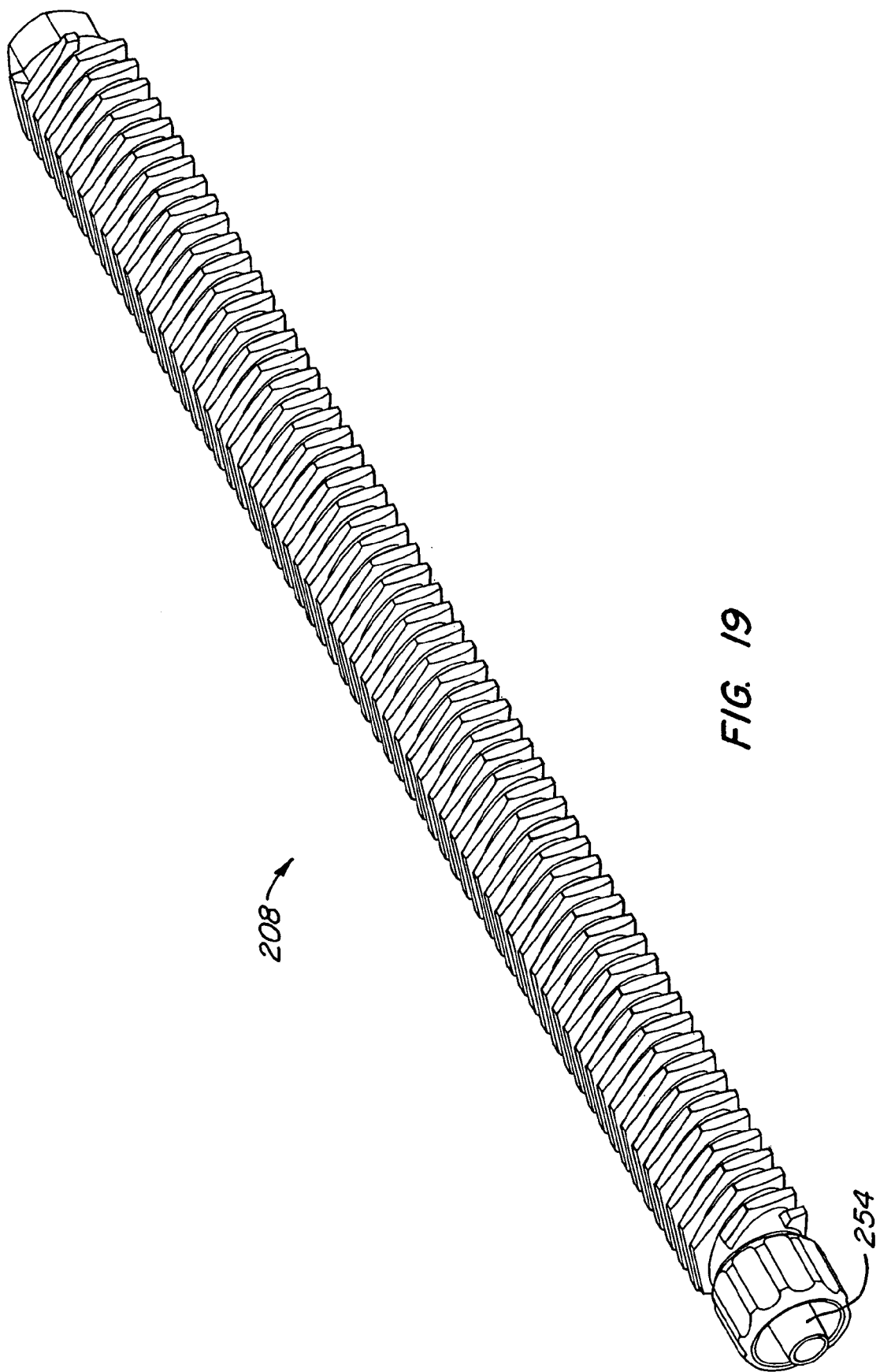
FIG. 19 is a perspective view of a cartridge for the tissue shaping device delivery system of FIG. 14.
Figure 20:
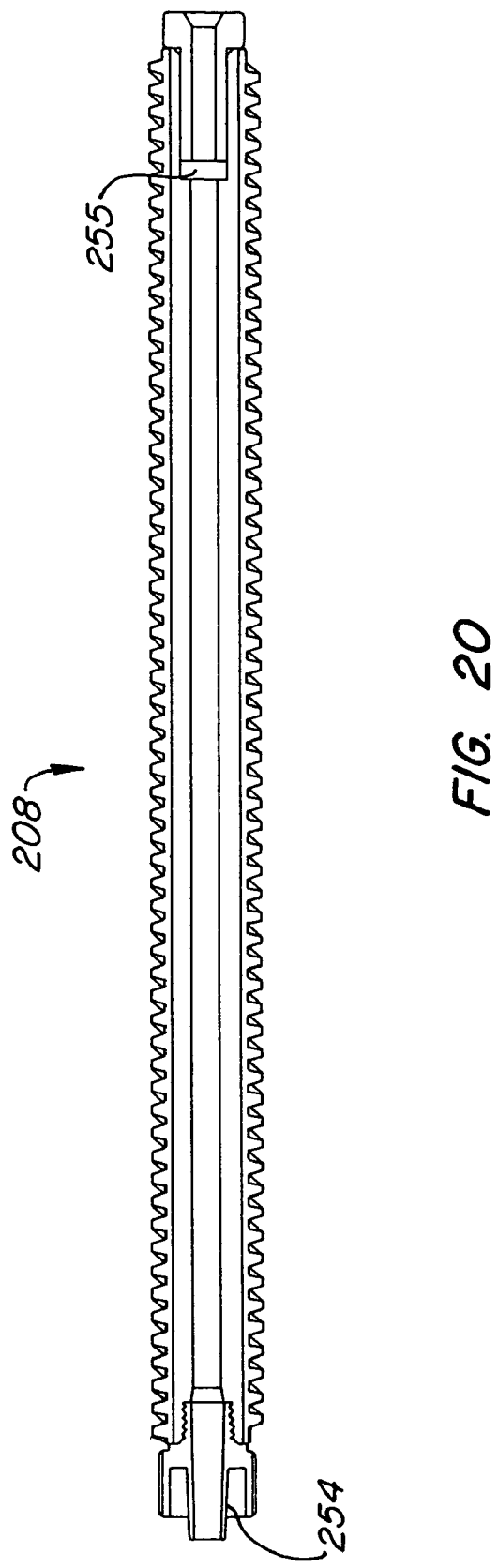
FIG. 20 is a cross-sectional view of the cartridge of FIG. 19.

Cartridge 208 is shown in more detail in FIGS. 19 and 20. Cartridge 208 has a central lumen 252 with a lubricious polymeric liner. The diameter of central lumen 252 may be substantially the same as the diameter of a delivery catheter to be used to deliver device 202. Alternatively, the diameter of central lumen 252 may be larger than the intended delivery catheter diameter to minimize stress on the tissue shaping device during sterilization, temperature changes during shipping, etc. Cartridge 208 has a male luer connector 254 at its distal end for mating with a corresponding female luer connector on the delivery catheter, as described below. The outside of the cartridge preferably has at least one flat side in order to prevent rotation of the cartridge with respect to the handle during deployment, as described below. In the embodiment shown in FIGS. 19 and 20, cartridge 208 has a hexagonal cross-section presenting six possible orientations for mating with a flat side formed on the inside of the handle during delivery and deployment of the tissue shaping device. An O-ring seal 255 at the proximal end of cartridge 208 seals around locking sleeve 220 to prevent backflow of blood or other fluids while still permitting relative movement between locking sleeve 220 and cartridge 208.

Figure 21:
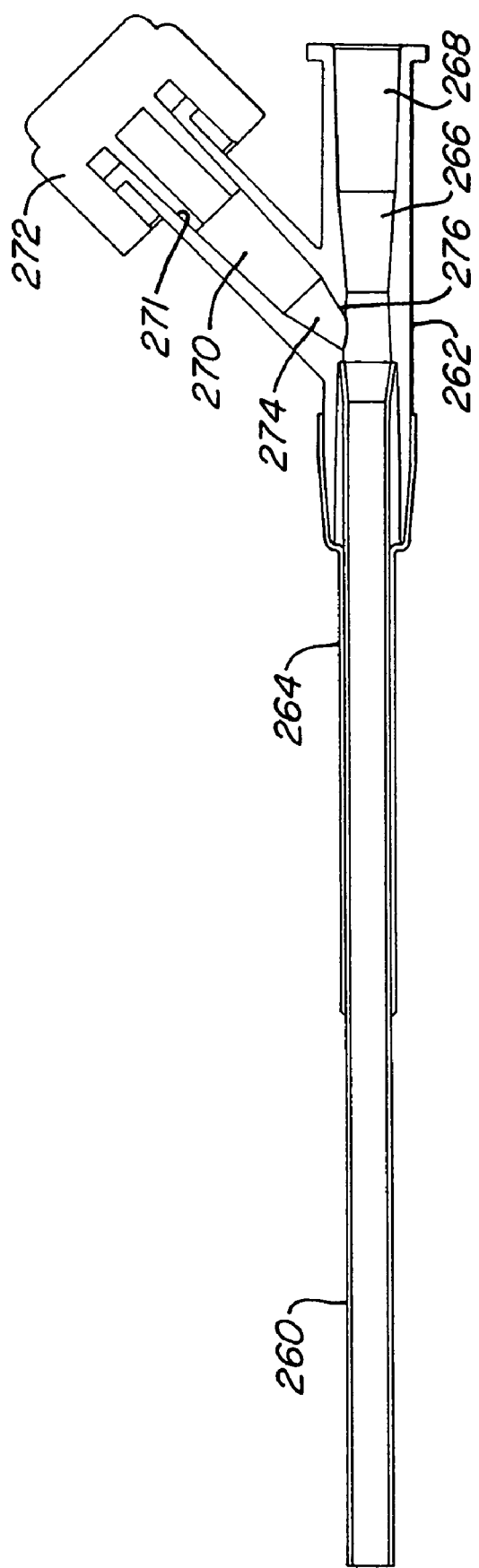
FIG. 21 is a cross-sectional view of a delivery catheter and connector for use with the tissue shaping device delivery system of FIGS. 14-20.

FIG. 21 shows a delivery catheter 260 and connector 262 for use with the cartridge and handle of this invention. The length and diameter of catheter 260 depends on the application. For example, to deliver a tissue shaping device to the coronary sinus through the jugular vein to treat mitral valve regurgitation, catheter 260 may be a nine french diameter catheter at least 65 cm. long. Catheter 260 may also have a radiopaque market on its distal end for visualization via fluoroscopy. When it needs to negotiate bends and turns to reach the target treatment site, catheter 260 may be more flexible at its distal tip than along its proximal end. Catheter 260 may also be braided to increase its compression strength, which aids in locking anchors, recapturing devices, etc., as described below.

Y-shaped connector 262 is attached to the proximal end of catheter 260 by adhesive and a shrink tube 264. Connector 262 has a main channel 266 with a female luer connection 268 adapted to mate with the luer connection of cartridge 208. A second channel 270 meets the main channel 266 proximal to the proximal end of delivery catheter 260. Second channel 270 also has a luer connection to permit it to be connected to a source of imaging contrast agent, such as dye. Second channel 270 enables a dye source to be connected and for dye to be injected even during use of the main channel to deliver and deploy the tissue shaping device. (The space between the inner diameter of the delivery catheter and the outer diameter of the locking sleeve permits contrast dye to flow distally to the target treatment site.) A cap 272 may be used to close off second channel 270 when not in use. The diameters of both channels transition down from the standard luer fitting size to the diameter of the delivery catheter.

A first step for using the tissue shaping system of this invention to treat mitral valve regurgitation is to access the coronary sinus of the patient's heart. One way of reaching the coronary sinus is to insert a sheath into the patient's jugular vein. A guide catheter with a precurved tip may then be inserted into the sheath and advanced to coronary sinus ostium within the right atrium of the heart. A guidewire may then be advanced through the guide catheter and into the coronary sinus, and the guide catheter may be removed from the patient, leaving the guidewire behind. The delivery catheter 260 may then be advanced along the guidewire, and the guidewire may be removed.

The anatomy of the heart varies from patient to patient. For example, the diameter and length of the coronary sinus are patient-dependent as well as the location of coronaries arteries that may pass between the coronary sinus and the heart. One optional method step, therefore, is to introduce dye or another imaging contrast agent into the coronary sinus through the delivery catheter (such as through the Y-shaped connector 262) to perform a venogram while performing an angiogram on the coronary arteries in a known manner. These images will identify the relative positions of the coronary sinus and coronary arteries and will give a relative indication of the length and diameter of the coronary sinus at the target treatment site.

In addition, in order to calibrate the venogram with the actual size of the imaged vessels, a marker catheter may be inserted into the coronary sinus through the delivery catheter during the venogram. The marker catheter has radiopaque markings a fixed distance apart. By measuring on the venogram the distance between markings on the marker catheter, a correction factor may be devised to correct the measured diameter and length of the coronary sinus. Alternatively, radiopaque markings may be added to the delivery catheter itself, thereby eliminating the need to insert a marker catheter to obtain the correction factor measurements. Dye may also be injected during delivery and deployment of the tissue shaping device for imaging purposes.

After removal of the marker catheter, the delivery system may be attached to the delivery catheter. Prior to the start of the procedure, locking sleeve 220 is in its proximal-most position so that locking sleeve actuator knobs 222 are in slots 242 of release knob 240, and screw down portion 223 is screwed against housing 226 to hold locking sleeve 220 in place. Pusher 210 and locking sleeve 220 extend from the distal end of handle 200 to the device 202 within cartridge 208. The lengths of pusher 210 and locking sleeve 220 correspond to the length of delivery catheter 260, as discussed below. Lengths of pusher 210 and locking sleeve 220 may be exposed between handle 200 and cartridge 208.

To begin delivering tissue shaping device 202 to the patient's coronary sinus, cartridge 208 (containing tissue shaping device 202) and delivery catheter 260 are then connected at luer connection 268 of the main channel of Y-connector 262. The distal tip of the delivery catheter is in place in the coronary sinus at the distal end of the target treatment site. To begin delivery of the device from cartridge 208 into delivery catheter 260, handle 200 is advanced distally toward cartridge 208 and delivery catheter 260. As the handle advances toward the cartridge and toward the patient, pusher 210 moves device 202 distally out of cartridge 208 into Y-connector 262 and then into delivery catheter 260. The structure of the point where the Y-connector's second channel 270 meets the main channel 266—specifically, reduced diameter portion 274 and tab 276—helps prevent the tissue shaping device from expanding and getting caught at the junction of the two channels.

In certain embodiments of the invention, the advancing handle 200 reaches cartridge 208 when or before device 202 reaches the distal end of delivery catheter 260. For example, in the embodiment shown in FIGS. 14-21, the relative lengths of device 202, pusher 210, handle 200 and delivery catheter 260 are such that the distal end of handle 200 reaches the proximal end of cartridge 208 before device 202 reaches the distal end of delivery catheter 260. After this point, further advancement of handle 200 places handle housing 226 around cartridge 208 so that cartridge 208 moves inside the handle. A flat interior surface (not shown) formed in handle 200 mates with one of the flat sides of cartridge 208 to prevent relative rotation between the cartridge and the handle as control nut 250 rotates.

In one embodiment, rotating control nut 250 is threaded onto cartridge 208 prior to use of the system to treat a patient, as shown in FIG. 14. The location of control nut 250 on cartridge 208 depends on the length of the device 202 within cartridge 208 as well as the relative lengths of the pusher and delivery catheter. In this embodiment, these elements are sized and configured so that control nut 250 engages with, and snaps to, the distal end of handle 200 at the point during device delivery when device 202 has reached the distal end of delivery catheter 260. This action engages cartridge 208 with handle 200 for controlled delivery and deployment of tissue shaping device 202. Alternatively, control nut 250 can be disposed on the distal end of handle 200 from the start. In this case, cartridge 208 engages handle 200 through control nut 250 as soon the proximal end of cartridge 208 reaches handle 200, which may be before device 202 has reached the distal end of delivery catheter 260.

After cartridge 208 engages handle 200 through control nut 250, all further relative movement between cartridge 208 and handle 200 is controlled by rotating control nut 208. When tissue shaping device 202 is at the distal end of catheter 260 at the distal end of the target treatment site (as determined fluoroscopically, e.g.) the physician ceases moving handle 200 toward the patient. Instead, handle 200 (and therefore device 202) is held stationary while cartridge 208 and delivery catheter 260 are pulled proximally by rotating control nut 250. This action exposes the device's distal anchor 204, which begins to self-expand. Control nut 250 is then rotated the other direction to advance delivery catheter 260 distally to apply a force to the proximal side of anchor 204 to further expand and lock the anchor, i.e., by advancing the anchor's lock loop over its lock bump, as described above. Thus, control nut 250 acts as an actuator for expanding and locking the device's distal anchor.

After locking the distal anchor, a proximal cinching force is applied to the device through tether 216 to reshape the mitral valve annulus by moving handle 200 proximally away from the patient, preferably while observing the status of the patient's mitral valve regurgitation and vital signs, such as described in U.S. patent application Ser. No. 10/366,585, "Method of Implanting a Mitral Valve Therapy Device." Contrast dye may be injected via connector 262 to visualize the anchor while cinching. When an appropriate amount of mitral valve regurgitation has been achieved, control nut 250 is rotated while holding handle 200 in place to pull delivery catheter 260 proximally with respect to tissue shaping device 202, thereby exposing proximal anchor 206, which begins to self-expand.

In one embodiment of the invention, locking sleeve 220 is used in place of the larger diameter delivery catheter to further expand and lock proximal anchor 206 in order to avoid inadvertent recapture of the proximal anchor by the delivery catheter. Screw down portion 223 of knobs 222 is loosened to permit knobs 222 to slide forward in tracks 224, thereby advancing locking sleeve 220 distally toward anchor 206. Locking sleeve 220 applies a distally directed force on the proximal side of anchor 206 to further expand and lock the anchor, i.e., by advancing the anchor's lock loop over its lock bump, as described above. Thus, knobs 222 act as an actuator for expanding and locking the device's proximal anchor. Expansion and locking of the proximal anchor maintains the cinching action and, therefore, the reduction in mitral valve regurgitation caused by the device's reshaping of the mitral valve annulus.

Alternatively, the delivery catheter can be used to expand and lock the proximal anchor in the same manner as the distal anchor.

The delivery system of this embodiment enables the tissue shaping device to be fully deployed before it is detached from the delivery system. If the tissue shaping device's placement is satisfactory, the device is unhitched from the delivery system. To unhitch, release knob 240 is rotated to move release knob and the attached hitch wire 218 proximally with respect to device 202. This action pulls the distal end of hitch wire 218 out of the device's proximal anchor crimp 207 and releases the looped end of tether 216, thereby disengaging device 202 from the delivery system. The delivery catheter, tether and hitch wire may then be removed from the patient.

The slots 242 in release knob 240 prevent rotation of release knob 240 when locking sleeve 220 is in its proximal-most position. This device release interlock feature helps ensure that the locking sleeve has been used to lock the proximal anchor before the tissue shaping device is disengaged from the delivery system.

In certain instances, after initial deployment but before disengaging the hitch wire and tether the tissue shaping device may need to be recaptured and either removed from the patient or deployed at a different site. In that case, locking sleeve 220 is advanced distally to the proximal side of proximal anchor 206 by moving knobs 222 forward in tracks 224. While holding handle 200 stationary to hold device 202 against distal movement through the action of tether 216, control nut 250 is rotated to advance delivery catheter 260 distally over locking sleeve 220 to and over proximal anchor 206, deforming anchor 206 so that it fits back inside catheter 260. In this manner, control nut 250 is used as a recapture actuator; use of the control nut to apply the recapture force helps prevent a sudden inadvertent distal advancement of the catheter when the anchor collapses and enters the catheter. Once the proximal anchor has been recaptured into the delivery catheter, the catheter is then advanced further distally to recapture distal anchor 204 in the same way. Device 202 can then be moved or removed from the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A tissue shaping system comprising:
   a tissue shaping device comprising an expandable anchor and a lock, wherein the expandable anchor has an unlocked delivery configuration and a locked configuration;
   a delivery catheter;
   a delivery mechanism adapted to deliver the tissue shaping device from outside a patient to a target site within a lumen within the patient via the delivery catheter; and
   an actuator that is configured and arranged to release the expandable anchor from the delivery catheter and is further configured and arranged to lock the expandable anchor in the locked configuration.

2. The tissue shaping system of claim 1 wherein the delivery mechanism comprises a pusher.

3. The tissue shaping system of claim 1 tissue shaping system further comprising a cartridge adapted to contain the tissue shaping device, the delivery mechanism being further adapted to deliver the tissue shaping device from the cartridge to the delivery catheter.

4. The tissue shaping system of claim 1 tissue shaping system further comprising a dye port adapted to admit an imaging contrast agent to the lumen.

5. The tissue shaping system of claim 4 wherein the delivery catheter and delivery mechanism are further adapted to permit delivery of imaging contrast agent from the dye port to the lumen during delivery and deployment of the tissue shaping device.

6. The tissue shaping system of claim 4 further comprising a connector extending from a proximal end of the delivery catheter, the connector comprising the dye port and a device port, the delivery mechanism being further adapted to deliver the tissue shaping device from outside the patient to the delivery catheter through the device port.

7. The tissue shaping system of claim 6 further comprising a cartridge adapted to contain the tissue shaping device and adapted to connect to the device port of the connector.

8. The tissue shaping system of claim 1 further comprising a handle associated with the delivery mechanism.

9. The tissue shaping system of claim 8 wherein the handle is adapted to support the actuator.

10. The tissue shaping system of claim 8 further comprising a cartridge adapted to contain the tissue shaping device.

11. The tissue shaping system of claim 10 wherein the cartridge is further adapted to engage the handle during delivery and/or deployment of the tissue shaping device.

12. The tissue shaping system of claim 1 wherein the actuator is further adapted to operate the delivery mechanism to move the tissue shaping device with respect to the delivery catheter.

13. The tissue shaping system of claim 12 wherein the actuator is further adapted to move the tissue shaping device with respect to the delivery catheter to expose the anchor.

14. The tissue shaping system of claim 12 wherein the actuator is further adapted to recapture the anchor into the delivery catheter.

15. The tissue shaping system of claim 12 wherein the actuator comprises a rotating nut.

16. The tissue shaping system of claim 1 wherein the actuator is adapted to move the delivery catheter distally to lock the anchor.

17. The tissue shaping system of claim 1 further comprising a locking sleeve, the actuator being further adapted to move the locking sleeve distally to lock the anchor.

18. The tissue shaping system of claim 1 further comprising an attachment mechanism adapted to attach the tissue shaping device to the delivery mechanism.

19. The tissue shaping system of claim 18 wherein the attachment mechanism comprises a tether attached to the tissue shaping device.

20. The tissue shaping system of claim 18 wherein the attachment mechanism is further adapted to release the tissue shaping device from the delivery mechanism.

21. The tissue shaping system of claim 20 wherein the attachment mechanism comprises a hitch wire and a tether attached to the tissue shaping device.

22. The tissue shaping system of claim 21 wherein the attachment mechanism further comprises a hitch wire actuator adapted to move the hitch wire to release the tether from the device.

23. The tissue shaping system of claim 20 further comprising a device release interlock adapted to prevent release of the device prior to actuating the anchor lock actuator.

24. The tissue shaping system of claim 1 wherein the anchor comprises a first anchor, the tissue shaping device further comprising a second anchor, the actuator being further adapted to deliver an actuation force to a second anchor lock to lock the second anchor in an expanded configuration.

25. The tissue shaping system of claim 1 wherein the anchor comprises a first anchor and the actuator comprises a first actuator, the tissue shaping device further comprising a second anchor and the tissue shaping system further comprising a second actuator, the second actuator being further adapted to deliver an actuation force to a second anchor lock to lock the second anchor in an expanded configuration.

26. The tissue shaping system of claim 25 further comprising a handle supporting the first and second actuators.

27. A system adapted to percutaneously deliver and deploy a tissue shaping device at a target site within a lumen of a patient, the system comprising:
a handle;
a delivery mechanism supported by the handle and adapted to deliver the tissue shaping device from outside the patient to the treatment site via a delivery catheter; and
an actuator supported by the handle that is configured and arranged to release the expandable anchor from the delivery catheter and is further configured and arranged to lock the expandable anchor in a locked configuration.

28. The system of claim 27 wherein the delivery system comprises a pusher supported by the handle.

29. The system of claim 27 wherein the handle comprises a cartridge interface adapted to mate with a cartridge containing a tissue shaping device.

30. The system of claim 29 wherein the delivery system is further adapted to deliver the tissue shaping device from a delivery catheter to the target site when a tissue shaping device cartridge engages the cartridge interface.

31. The system of claim 30 wherein the actuator comprises the cartridge interface.

32. The system of claim 31 wherein the actuator comprises a rotating member comprising threads adapted to mate with threads on a cartridge.

33. The system of claim 30 wherein the actuator comprises a rotating member, the cartridge interface comprising threads on the rotating member adapted to mate with threads on the cartridge.

34. The system of claim 27 further comprising a locking sleeve, the actuator being further adapted to move the locking sleeve distally to lock the anchor.

35. The system of claim 34 wherein the handle comprises a channel, the actuator being disposed in the channel.

36. The system of claim 35 wherein the actuator comprises an actuator lock adapted to prevent movement of the actuator within the channel.

37. The system of claim 27 further comprising a device attachment mechanism supported by the handle and adapted to attach the tissue shaping device to the handle.

38. The system of claim 37 wherein the attachment mechanism comprises a tether attached to the handle.

39. The system of claim 37 wherein the attachment mechanism comprises a hitch wire attached to the handle.

40. The system of claim 39 wherein the attachment mechanism further comprises a hitch wire actuator adapted to move the hitch wire to release the device.

41. The system of claim 40 further comprising a device release interlock adapted to prevent operation of the hitch wire actuator prior to actuating the anchor lock actuator.

42. The tissue shaping system of claim 1 wherein the actuator is configured and arranged to control movement of the delivery catheter.

43. The tissue shaping system of claim 42 wherein the actuator is configured and arranged to retract the delivery catheter in a proximal direction to allow the expandable anchor to be released from the delivery catheter.

44. The tissue shaping system of claim 43 wherein the actuator is configured and arranged to advance the delivery catheter in a distal direction to lock the expandable anchor in the locked configuration.

45. A tissue shaping system comprising:
a tissue shaping device comprising an expandable anchor and an elongate member extending from the expandable anchor, wherein the expandable anchor has a collapsed delivery configuration and a locked configuration;
a handle;
a delivery catheter; and
an actuator supported by the handle that is configured and arranged to release the expandable anchor from the delivery catheter and is further configured and arranged to lock the expandable anchor in the locked configuration.

46. The tissue shaping system of claim 45 wherein the actuator is configured and arranged to control movement of the delivery catheter.

47. The tissue shaping system of claim 46 wherein the actuator is configured and arranged to retract the delivery catheter in a proximal direction to allow the expandable anchor to be released from the delivery catheter.

48. The tissue shaping system of claim 47 wherein the actuator is further configured and arranged to advance the delivery catheter in a distal direction to lock the expandable anchor in the locked configuration.

* * * * *